United States Patent [19]

John et al.

[11] 4,176,130
[45] Nov. 27, 1979

[54] PROCESS FOR PREPARING ACYLOXYSILANES AND ACYLOXYSILOXANES

[75] Inventors: Peter John, Burghausen, Fed. Rep. of Germany; Wolfgang Feichtner, Ach, Austria; Werner Graf; Volker Frey, both of Burghausen, Fed. Rep. of Germany

[73] Assignee: Wacker-Chemie GmbH, Munich, Fed. Rep. of Germany

[21] Appl. No.: 974,200

[22] Filed: Dec. 28, 1978

[30] Foreign Application Priority Data

Jan. 17, 1978 [DE] Fed. Rep. of Germany ....... 2801780

[51] Int. Cl.$^2$ .............................................. C07F 7/08
[52] U.S. Cl. ............................................. 260/448.2 E
[58] Field of Search ................................ 260/448.2 E

[56] References Cited

U.S. PATENT DOCUMENTS

| | | | |
|---|---|---|---|
| 3,974,198 | 8/1976 | Ashby | 260/448.2 E |
| 4,028,391 | 6/1977 | Foley | 260/448.2 E X |
| 4,066,680 | 4/1978 | Lewis et al. | 260/448.2 E |

OTHER PUBLICATIONS

"Chemical Abstracts", 77, 153525q, 1972.

*Primary Examiner*—Paul F. Shaver

[57] ABSTRACT

This invention relates to an improved process for preparing acyloxysilanes and acyloxysiloxanes which comprises conducting an aliphatic carboxylic acid in vapor form upwards from the bottom of a column countercurrent to the flow of a chlorosilane in which the carboxylic acid is introduced into the column at such a rate that the carboxylic acid does not exceed about 1.3 mol per gram atom of Si-bonded chlorine in the column while removing the acyloxysilane from the bottom of the column.

The acyloxysiloxanes are prepared by conducting an aliphatic carboxylic acid upwards from the bottom of a column in vapor form countercurrent to the flow of a chlorosilane while introducing up to about 10 percent by weight of water based on the weight of the carboxylic acid into the column and removing the acyloxysiloxane from the bottom of the column.

7 Claims, No Drawings

PROCESS FOR PREPARING ACYLOXYSILANES AND ACYLOXYSILOXANES

The present invention relates to the preparation of silanes and siloxanes and more particularly to a process for preparing acyloxysilanes and acyloxysiloxanes.

BACKGROUND OF INVENTION

Acyloxysilanes and acyloxysiloxanes are well known and have been prepared heretofore by reacting in a column at an elevated temperature, a chlorosilane and an aliphatic carboxylic acid. U.S. Pat. No. 3,974,198 to Ashby discloses an improved process for preparing acyloxysilanes by reacting a chlorosilane with a carboxylic acid or carboxylic acid anhydride in the presence of an iron complexing agent. In comparison to the process disclosed in U.S. Pat. No. 3,974,198, the process of this invention can be carried out in the absence of iron or iron complexing agents. In addition, the process of this invention can be conducted in the absence of expensive solvents and with a very short reaction time. Moreover, excellent yields of acyloxysilanes are obtained having a very low concentration of acyloxysiloxanes. Also, acyloxysiloxanes prepared in accordance with the process of this invention have the advantage that they are not contaminated with iron compounds which have a tendency to impart discolorations thereto.

A process is also described in Chemical Abstracts, Volume 77, 1972, page 70, (153525q) for preparing acyloxysiloxanes which comprises partially hydrolyzing acyloxysilanes in the presence of tetrahydrofuran. In contrast to the process described in Chemical Abstracts, the process of this invention has the advantage that it does not require the use of tetrahydrofuran and it does not require the preparation of the acyloxysilane in a separate step prior to the formation of the acyloxysiloxanes.

Therefore it is an object of the present invention to provide an improved process for preparing acyloxysilanes. Another object of this invention is to provide an improved process for preparing acyloxysiloxanes. Still another object of this invention is to provide an improved process for preparing acyloxysilanes and acyloxysiloxanes in the absence of organic solvents. A further object of this invention is to provide an improved process for preparing acyloxysiloxanes in a single step from chlorosilanes and carboxylic acids. A still further object of this invention is to provide an improved process for preparing acyloxysilanes and acyloxysiloxanes in the absence of iron and iron complexing agents.

SUMMARY OF INVENTION

The foregoing objects and others which will become apparent from the following description are accomplished in accordance with this invention, generally speaking, by providing an improved process for preparing acyloxysilanes and acyloxysiloxanes by reacting chlorosilanes with aliphatic carboxylic acids in a column at an elevated temperature, the improvement which comprises conducting an aliphatic carboxylic acid in vapor form upwards from the bottom of a column countercurrent to the flow of the chlorosilane in which the aliphatic carboxylic acid is introduced into the column at such a rate that it does not exceed 1.3 mol per gram atom of Si-bonded chlorine in the column while removing the acyloxysilane from the bottom of the column.

In the preparation of the acyloxysiloxanes up to about 10 percent by weight of water based on the weight of the aliphatic carboxylic acid is introduced into the column and the corresponding acyloxysiloxane is recovered from the bottom of the column.

DETAILED DESCRIPTION OF INVENTION

Chlorosilanes which may be used in the process of this invention are those of the general formula:

$$R_aSiCl_{4-a}$$

where R represents the same or different substituted and unsubstituted hydrocarbon radicals having from 1 to 8 carbon atoms, and a is 0, 1, 2, or 3.

Examples of hydrocarbon radicals represented by R are alkyl radicals, such as the methyl, ethyl, isopropyl, sec-butyl and 2-ethylhexyl radicals; alkenyl radicals such as the vinyl, and allyl radicals, as well as the hexadienyl radicals; cycloalkyl radicals, such as the cyclopentyl and the cyclohexyl radicals; cycloalkenyl radicals such as cyclopentenyl, cyclohexenyl and ethylcyclohexenyl radicals; aromatic hydrocarbon radicals, such as the phenyl radical; aralkyl radicals such as the benzyl and phenylethyl radicals; and alkaryl radicals such as the tolyl and dimethylphenyl radicals. Examples of substituted hydrocarbon radicals represented by R are halogenated hydrocarbon radicals such as the chloromethyl, 3-chloropropyl and 3,3,3-trifluoropropyl radicals.

Other chlorosilanes which may be employed in the process of this invention are those of the general formula:

$$Cl_{3-b}SiR_bR^1R_bSiCl_{3-b}$$

where R is the same as above, $R^1$ represents a bivalent hydrocarbon radical, for example an ethylene or phenylene radical and b is 1 or 2.

The carboxylic acids used in the process of this invention may be acetic acid, propionic acid, butyric acid or dimethylacetic acid.

The aliphatic carboxylic acid is preferably employed in an amount of at least 1 mol per gram atom of Si-bonded chlorine in the chlorosilane.

It is preferable that the rate of addition of the carboxylic acid into the column be regulated by means of a device which is controlled by the temperature prevailing in the bottom one-third of the column.

The column used for the process of this invention may be any packed column which can also be used for fractionation distillations. It is preferred that the chlorosilane be introduced at a point in the column at least 90 cm above the point where the carboxylic acid is introduced. This means that the column is preferably at least 90 cm in height. The upper limit of the column's height is limited solely by economic considerations.

In the process of this invention, the reaction of the chlorosilane with aliphatic carboxylic acid may be carried out at atmospheric pressure, i.e., at 760 mm Hg (abs) or approximately 760 mm Hg (abs). However in order to obtain acyloxysilanes and/or acyloxysiloxanes which are substantially free of unreacted carboxylic acid and hydrogen chloride, it is preferred that the reaction be carried out at 10 to 600 mm Hg (abs) and, more preferably from 50 to 300 mm Hg (abs).

The chlorosilane is reacted with the aliphatic carboxylic acid at a temperature which corresponds or substantially corresponds to the boiling point of the carboxylic acid used under the prevailing conditions of pressure.

If water is employed in the process of this invention to prepare acyloxysiloxanes, then it may be introduced into the column at any location in which solid hydrolyzates will not form. However, it is preferred that the water be mixed with the carboxylic acid. When water is used in the process, then it is preferably employed at the rate of at least 0.5 percent by weight, based on the weight of the carboxylic acid.

The use of a solvent which is inert to the reactants is neither desirable nor required, but it is by no means to be excluded. Examples of solvents which may be used with the process of this invention are toluene and methylene chloride.

It is preferred that the process of this invention be carried out as a continuous process.

Acyloxysilanes having the general formula:

$$R_aSi(OCOR')_{4-a}$$

are prepared by the process of this invention using chlorosilanes of the formula $$R_aSiCl_{4-a}$$

where R and a are the same as above and R' represents the methyl, ethyl, propyl or isopropyl radicals.

The acyloxysilanes and acyloxysiloxanes prepared in accordance with this invention may be employed in all applications where acyloxysilanes and acyloxysiloxanes have been used heretofore, i.e., they may be mixed with diorganopolysiloxanes having terminal Si-bonded hydroxyl groups to prepare compositions which may be stored under anhydrous conditions but when exposed to water at room temperature cure to elastomeric solids.

The following examples illustrate the process of this invention and should not be construed as limiting the invention thereto.

EXAMPLE 1

A 3.5 meter long glass tube having an inside diameter of 100 mm, which is filled with 8 mm Raschig rings, is used as a column. The top of the column is connected to a reflux condenser which is cooled with an aqueous solution of sodium chloride having a temperature of −20° C. About 400 ml per hour of ethyltrichlorosilane is introduced into the center of the column. Slightly above the bottom of the column, 550 ml per hour of glacial acetic acid is introduced into the column and a control element which is connected to a temperature sensing device operates a pump which supplies the glacial acetic acid to the column so as to maintain the temperature in an electrically heated forced circulation evaporator at approximately 135° C. The pressure in the column is 120 mm Hg (abs) so that the glacial acetic acid evaporates as soon as it enters the column and rises against the flow of ethyl trichlorosilane. Ethyltriacetoxysilane is continuously removed from the bottom of the column.

| Yield: | 98 weight percent of theoretical |
|---|---|
| Ethyltriacetoxysilane content: | 94 weight percent |
| Acetic acid content: | 2 weight percent |
| HCl content: | less than 50 ppm by weight |

EXAMPLE 2

A 3.5 meter long glass tube having an inside diameter 100 mm, which is filled with 8 mm Raschig rings is used as a column. The top of the column is connected to a reflux condenser which is cooled with an aqueous solution of sodium chloride having a temperature of −20° C. About 250 ml per hour of methyltrichlorosilane is introduced approximately at the center of the column. About 220 ml per hour of acetic acid containing 4 percent by weight of water based on the weight of acetic acid is introduced at a point slightly above the bottom of the column. A control element which is connected to a temperature sensing device controls the pump which pumps the acetic acid into the column so as to maintain the temperature in an electrically operated forced circulation evaporator at approximately 130° C. Pressure within the column is approximately 135 mm Hg (abs) so that the acetic acid evaporates immediately after it enters the column and rises against the methyltrichlorosilane.

A mixture of methylacetoxysiloxanes which does not cyrstallize at room temperature and whose principal component is 1,3-dimethyl-1,1,3,3-tetraacetoxydisiloxane is continuously removed from the bottom of the column.

EXAMPLE 3

The process described in Example 1 is repeated, except that the glacial acetic acid is contaminated with 100 ppm of FeCl$_3$. The yield is again about 98 weight percent of theoretical. The ethyltriacetoxysilane content of the product has decreased slightly, i.e., to 92.5 percent by weight.

What is claimed is:

1. A process for preparing acyloxysilanes by reacting a chlorosilane with an aliphatic carboxylic acid in a column at an elevated temperature, the improvement which comprises passing an aliphatic carboxylic acid in the vapor phase upwards from the bottom of the column countercurrent to the flow of the chlorosilane, in which the aliphatic carboxylic acid is introduced into the column at such a rate that the carboxylic acid does not exceed 1.3 mol per gram atom of Si-bonded chlorine in the column while removing the acyloxysilane at the bottom of the column.

2. The process of claim 1, wherein the amount of the carboxylic acid introduced into the column is controlled by a temperature-governing device which is located in the lower one-third of the column.

3. The process of claim 1, wherein the reaction between the chlorosilane and the aliphatic carboxylic acid is carried out at 50 to 300 mm Hg (abs).

4. A process for preparing acyloxysiloxanes by reacting a chlorosilane with an aliphatic carboxylic acid in a column at an elevated temperature, the improvement which comprises passing an aliphatic carboxylic acid in the vapor phase upwards from the bottom of the column countercurrent to the flow of the chlorosilane in which the aliphatic carboxylic acid is introduced into the column at such a rate that the carboxylic acid does not exceed 1.3 mol per gram atom of Si-bonded chlorine in the column while simultaneously introducing into the column up to 10 percent by weight of water based on the weight of the aliphatic carboxylic acid and removing the acyloxysiloxane from the bottom of the column.

5. The process of claim 4, wherein the amount of the carboxylic acid introduced into the column is controlled by a temperature-governing device which is located in the lower one-third of the column.

6. The process of claim 4, wherein the reaction between the chlorosilane and the aliphatic carboxylic acid is carried out at 50 to 300 mm Hg (abs).

7. The process of claim 4, wherein the water is mixed with the carboxylic acid.

* * * * *